United States Patent [19]

Berry

[11] 4,152,600

[45] May 1, 1979

[54] NUCLEAR RADIATION MOISTURE GAUGE CALIBRATION STANDARD

[75] Inventor: Richard L. Berry, Raleigh, N.C.

[73] Assignee: Troxler Electronic Laboratories, Inc., Raleigh, N.C.

[21] Appl. No.: 734,624

[22] Filed: Oct. 21, 1976

[51] Int. Cl.$^2$ .............................................. G02B 5/00
[52] U.S. Cl. ................................... 250/505; 250/252; 250/390
[58] Field of Search ............... 250/252, 253, 390, 391, 250/505

[56] References Cited

U.S. PATENT DOCUMENTS

| | | | |
|---|---|---|---|
| 3,681,595 | 8/1972 | Dahlin | 250/252 |
| 3,867,638 | 2/1975 | Golden | 250/252 X |

*Primary Examiner*—Davis L. Willis
*Attorney, Agent, or Firm*—Bell, Seltzer, Park & Gibson

[57] ABSTRACT

A hydrophobic standard for calibrating nuclear radiation moisture gauges. In accordance with this invention, each standard has physical characteristics and dimensions effective for representing to a nuclear gauge undergoing calibration an infinite mass of homogeneous hydrogen content. Calibration standards are disclosed which are suitable for use with surface gauges and with depth gauges.

16 Claims, 10 Drawing Figures

U.S. Patent  May 1, 1979  Sheet 2 of 2  4,152,600
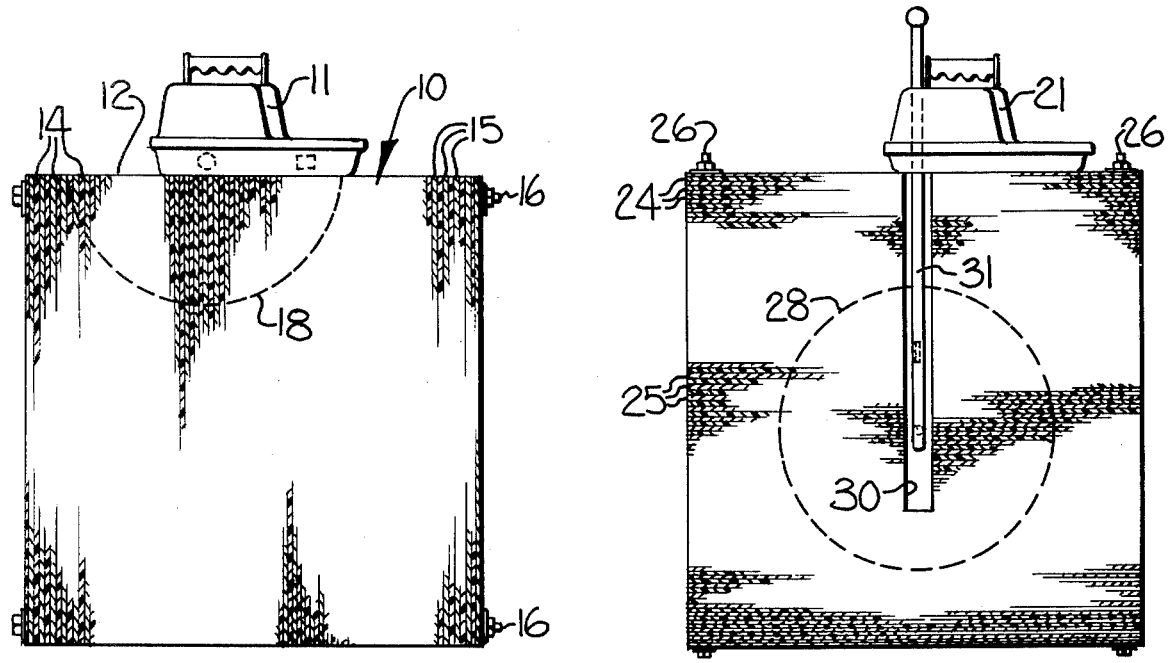
Fig-8
Fig-9
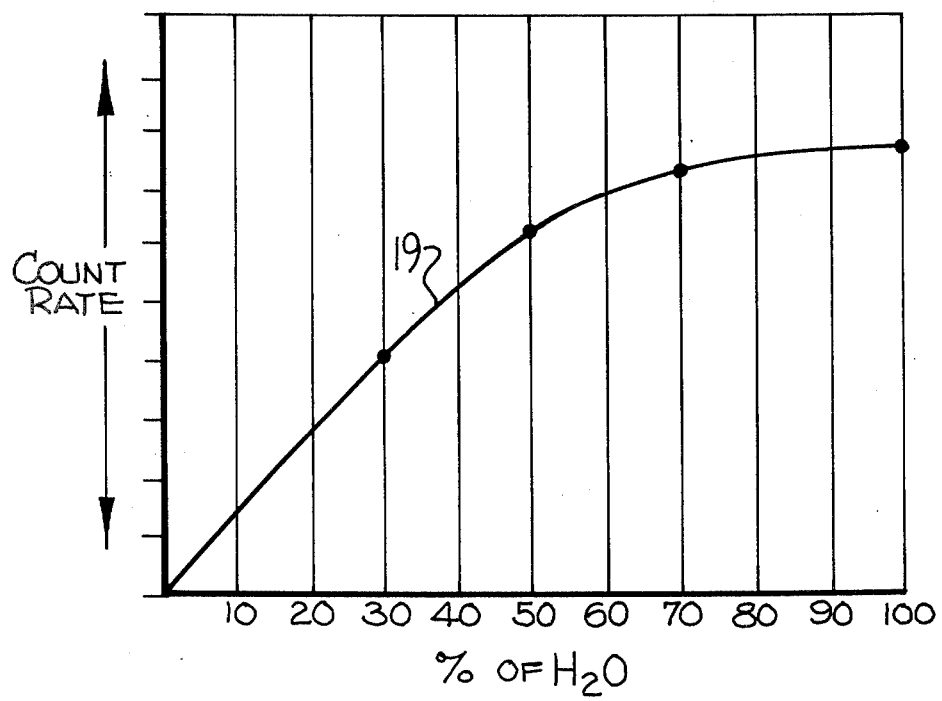
Fig-10

NUCLEAR RADIATION MOISTURE GAUGE CALIBRATION STANDARD

It has been known heretofore to determine the moisture content of soil through the use of a nuclear radiation gauge. In the most common form, such gauges employ fast (fission) neutrons directed into soil undergoing test. Whenever such neutrons collide with hydrogen atoms, such as in water, a certain statistically determinable fraction are slowed down or moderated to a remarkable extent by the inelastic collisions. These slow (thermal) neutrons are detected by an appropriate detector responsive to neutrons in a selected energy band. Neutrons detected by the detector are counted, with the count rate recorded indicating the soil moisture content. Soil moisture content has been indicated in terms of volume percent of the soil sample probed by the neutrons, in pounds per cubic foot, in inches of water per foot, and in other selected measures.

As will be appreciated by persons familiar with nuclear radiation gauge measurements, it is desirable to have such a gauge calibrated in terms of count rate and the selected measure of moisture content. Further, the typical non-linear response characteristic of a nuclear radiation gauge makes it highly desirable to have more than one calibration point for establishing a calibration curve to be used in determining moisture content from count rate.

Heretofore, it has been possible to establish a 100 percent water content calibration point by positioning a nuclear radiation moisture gauge of the surface or depth type to detect the moisture content of a body of water, such as might be held in a barrel or tub. Many attempts have been made to establish other calibration points through the use of various proposed standards containing less than 100 percent moisture. However, such attempts have not heretofore accomplished reliable calibration.

More particularly, prior proposed moisture standards have included such arrangements as a body of sand of known weight and/or volume contained within a barrel, tub or the like and to which a quantity of water of known weight and/or volume has been added. Another approach has relied upon the use of plaster or a similar material to retain a granulated material containing hydrogen in the molecular structure thereof, such as pellets or flakes of a hydrocarbon polymer. In such a proposed standard, the ratio of plaster to the material containing hydrogen is manipulated to approximate a moisture content of a desired percentage.

The difficulty encountered with such prior proposed calibration standards has been that the moisture content thereof has been neither reliably maintainable nor homogeneous. All such prior proposed calibration standards are hydrophillic, meaning that the actual moisture content will vary with ambient conditions. Should such a calibration standard be maintained in an ambient atmosphere of relatively high humidity, the moisture content of the calibration standard rises. Conversely, should the calibration standard be maintained in an ambient atmosphere of relatively low humidity, the moisture content drops. With fluctuating ambient conditions, the moisture content of the standard fluctuates in an unpredictable manner. The failure of a standard subject to such fluctuations to effectively function as a calibration standard will be easily appreciated by persons familiar with the art of calibrating instruments.

Recognizing the difficulties encountered heretofore, it is an object of the present invention to provide a hydrophobic standard means for calibrating nuclear radiation moisture gauges. In realizing this object of the present invention, a standard is proposed, designed and used which has little or no affinity for water and accordingly will not take up or give off water under ambient conditions of fluctuating humidity in such a manner as to change the effective percentage of hydrogen content represented to a nuclear gauge undergoing calibration.

Yet a further object of this invention is to provide a hydrophobic calibration standard for nuclear radiation moisture gauges formed by a body of superposed interleaved thin layers of a moderating material containing hydrogen in the molecular structure thereof and of a substantially non-moderating material. In realizing this object of the present invention, the body of superposed interleaved thin layers has physical characteristics effective for representing a mass of homogeneous hydrogen content to a nuclear gauge undergoing calibration. Further, the physical dimensions of the body are effective for representing an infinite mass to a nuclear gauge undergoing calibration.

Yet a further object of this invention is to provide standards in accordance with this invention adaptable for use with surface gauges, as well as to provide standards adaptable for use with depth gauges. In realizing this object of the present invention, it is contemplated that bodies of material prepared in accordance with the present invention may have a planar surface for receiving a surface gauge. Further, a body of material prepared in accordance with this invention may alternatively have a bore therein for receiving a depth gauge.

Yet a further object of the present invention is the provision of a plurality of bodies, each effective for representing a corresponding, discrete hydrogen content to a nuclear gauge undergoing calibration. In accordance with this object of the present invention, a plurality of calibration points at varying hydrogen contents are provided, thereby facilitating the plotting of a calibration curve for a particular nuclear radiation gauge undergoing calibration.

Some of the objects of the invention having been stated, other objects will appear as the description proceeds, when taken in connection with the accompanying drawings, in which:

FIG. 8 is an elevation view, taken substantially as indicated by the line 8—8 in FIG. 1, showing a surface gauge undergoing calibration;

FIG. 9 is a view similar to FIG. 8, taken substantially along the line 9—9 in FIG. 2 and illustrating a depth gauge undergoing calibration; and FIG. 10 is a schematic representation of a calibration curve as obtained through use of the calibration standards of the present invention.

While the hydrophobic calibration standard means of the present invention will be described hereinafter with particular reference to the accompanying drawings, it is to be understood from the beginning of this description that the description is directed primarily to the best form presently contemplated for this invention. However, it is known that the specific material choices or manner or assembly may be varied from those to be described hereinafter and the description of preferred forms is accordingly not to be taken as limiting on this invention. Instead, the description is to be taken as a broad teaching directed to persons skilled in the applicable nuclear radiation gauging technology.

Figure 1:
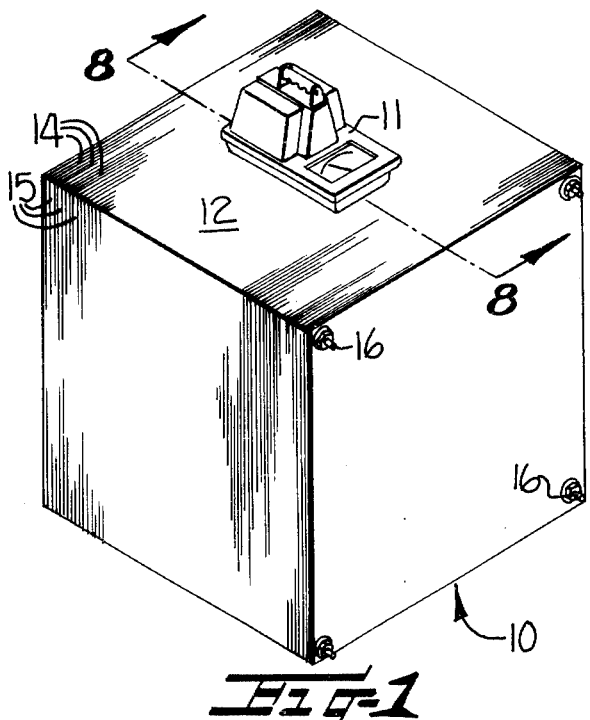
FIG. 1 is a perspective view of a hydrophobic calibration standard in accordance with the present invention, illustrating a surface gauge in place on the standard for calibration.

Referring now more particularly to the accompanying drawings, a hydrophobic calibration standard is generally indicated at 10 in FIG. 1. As there shown and will be described hereinafter, the calibration standard 10 is particularly intended for use with a nuclear radiation surface gauge 11 capable of determining the moisture content of a surface layer of soil. The structure and operation of the gauge 11 are known to persons skilled in the art of nuclear radiation material testing and accordingly will not be described in detail here.

In accordance with the present invention, the standard 10 is hydrophobic, meaning that it has little or no affinity for water. Having no affinity for water, the effective hydrogen content of the standard does not fluctuate with fluctuations in ambient conditions of moisture or humidity, thereby providing for the first time a reliable calibration standard for nuclear radiation moisture gauges. The physical characteristics of the standard 10 are such that the standard is effective for representing a mass of homogeneous hydrogen content to the gauge 11 undergoing calibration. Further, the physical dimensions of the standard 10 are such that it is effective for representing an infinite mass to the nuclear gauge 11. As illustrated in FIGS. 1 and 8, the standard 10 comprises a body of material having a planar surface 12 for receiving the surface guage 11.

Referring now more particularly to the physical characteristics of the standard 10 which render it effective for representing a mass of homogeneous hydrogen content to a gauge 11, the standard 10 comprises a body of superposed interleaved thin layers 14 of a moderating material containing hydrogen in the molecular structure thereof and thin layers 15 of a substantially non-moderating material. The interleaved nature of the layer is made more clear in FIGS. 3—7, to which attention is now directed. As used herein, the terms "moderating" and "non-moderating" refer to the characteristics of a material as providing inelastic collisions with fast neutrons which result in slow neutrons having energy in the ranges detected by the moisture gauge detector element. A moderating material slows fast neutrons in a manner similar to water contained in soil. A non-moderating material does not slow neutrons, in a manner similar to the common mineral content of soil.

In accordance with the present invention, the use of moderating material and substantially non-moderating material in thin layers accomplishes a substantially uniform distribution of moderating material throughout the body of material forming the standard 10, thereby imparting to the standard the characteristic of representing a mass of homogeneous hydrogen content. The extent of hydrogen content represented may be controlled by varying the effective thickness of the layers, or the respective proportions of moderating and non-moderating material. FIGS. 4—7 illustrate various approaches to achieving such varying distributions.

Figure 2:
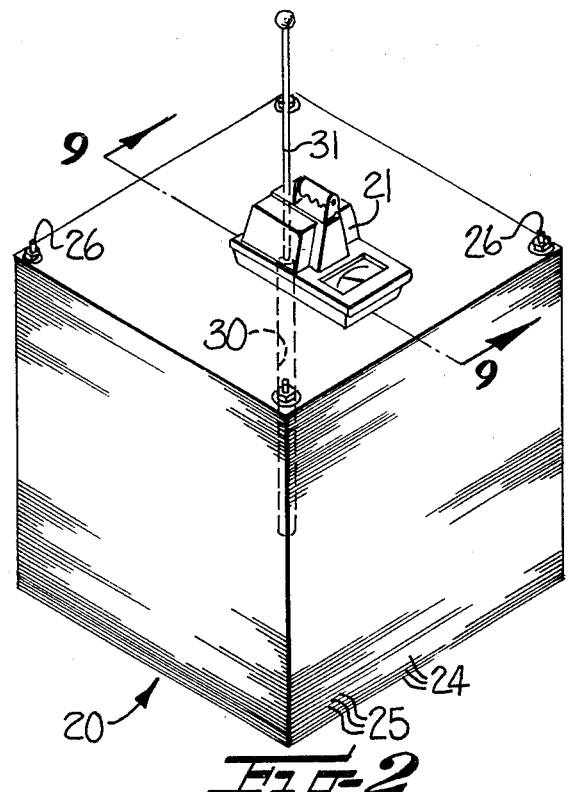
FIG. 2 is a view similar to FIG. 1, illustrating a depth gauge in position for calibration.
Figure 3:
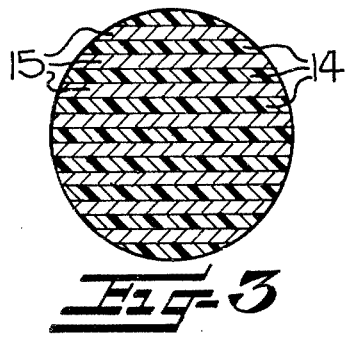
FIG. 3 is an enlarged sectional view of a hydrophobic calibration standard in accordance with the present invention, illustrating a particular arrangement of superposed interleaved thin layers of a moderating material and of a substantially non-moderating material.
Figure 4:
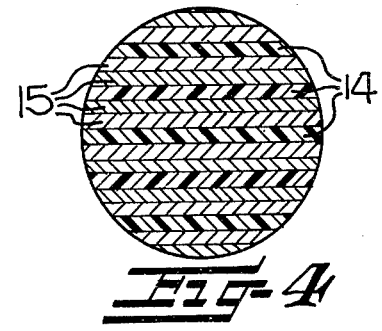
FIGS. 4–7 are views similar to FIG. 3, illustrating variations in the construction of hydrophobic calibration standards in accordance with the present invention.

Referring now more specifically to FIG. 2, it is to be noted that the thin layers 14 of moderating material and layers 15 of non-moderating material have a substantially common thickness. In preferred embodiments of a standard 10 in accordance with this invention, the material forming the thin layers 14 of moderating material preferably is a hydrocarbon polymer effective for moderating neutrons. A preferred polymer has been polyethylene, which may be purchased readily in films or sheets of desired gauges or thicknesses on the order of 20 mils or more or less. The thin layers 15 of non-moderating material have been, in preferred forms of this invention, magnesium metal which can be purchased in sheets having a thickness substantially the same if not identical to the thickness of the polyethylene film or sheet to be used. Other choices for the moderating and non-moderating material will be apparent to persons knowledgeable in nuclear radiation gauging techniques.

In assemblying the standard 10, the thin layers 14, 15 of moderating and non-moderating materials are cut from a supply of those materials, preferably to have common dimensions. The layers are stacked one on the other, clamped into a stacked relation, and then drilled to receive fastner means in the form of mounting bolts 16 which extend through four corners of the body of interleaved superposed layers. The bolts are drawn snug to maintain the thin layers in tightly engaging relation and the standard may then be placed in use.

In choosing the physical dimension of the layers 14, 15 to be assembled into the standard 10, it is desirable to have in mind the characteristics of operation of the gauges to be calibrated. Referring now more particularly to FIG. 8, a phantom line 18 has there been included to illustrate the effective half-spherical volume in which moderation of neutrons occurs during calibration of the surface gauge 11. As is known to persons skilled in the art of calibrating nuclear radiation moisture gauges, the statistics of neutron moderation predict that no neutron passing beyond a certain distance from the radiation source before being reduced to the energy level detectable will be reflected or scattered back to the detector. Knowing of this characteristic of the nuclear radiation gauging process, it is not necessary that the standard 10 be made of infinite size. However, it is highly desirable that the body of material forming the standard 10 be so sized that it is effective for representing an infinite mass to a nuclear gauge undergoing calibration. Stated differently, the physical dimensions of the standard 10 must be such as to entirely contain the part spherical volume 18 within which neutron moderation will occur. Thus, the exact physical dimensions of the standard 10 may vary somewhat depending upon the relative hydrogen content which the specific calibration standard has been designed to be effective as representing. For surface gauges, the convenient size is to form the layers 14, 15 to be approximately one meter square.

Figure 5:
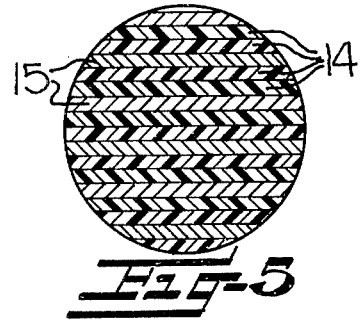
Figure 6:
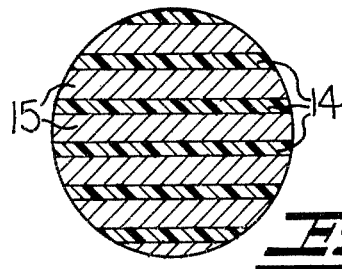
Figure 7:
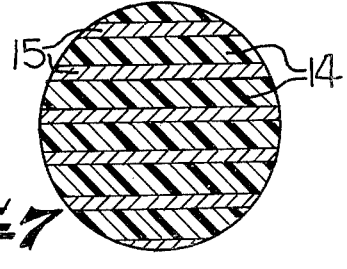

Referring now more particular to FIGS. 4–7, FIG. 4 illustrates an arrangement wherein the number of layers of non-moderating material 15 is twice the number of the layers of moderating material 14, so that layers of the moderating material 14 are sandwiched between sets of multiple adjacent layers of non-moderating material 15. As will be appreciated, such an arrangement yields a standard effective for representing a lower hydrogen content than with the standard of FIG. 3. FIG. 5 shows an arrangement somewhat similar to FIG. 4 in that the number of layers of one material is a multiple of a number of layers of the other material. However, in the arrangement of FIG. 5 it is the layers of non-moderating material which are sandwiched between sets of multiple adjacent layers of moderating material, yielding a standard which would represent a higher hydrogen content than the arrangement of FIG. 3. Results somewhat similar to those of FIGS. 4 and 5 may also be obtained by arrangements as illustrated in FIGS. 6 and 7, where the layers of moderating material 14 have a substantially constant, substantially uniform first thickness and the layers 15 of non-moderating material have a substantially constant, substantially uniform second thickness differing from the first thickness. As will be apparent, the thicker layer may be either the non-moderating layer (FIG. 6) or the moderating layer (FIG. 7).

Referring now to FIG. 10, it will be appreciated that a calibration curve 19 plotted for a nuclear radiation gauge through the use of calibration standard means in accordance with the present invention may be most readily determined where a plurality of points therealong are determinable from the standard means. In the particular calibration curve shown, standards have been employed in determining count rates indicative of moisture content at 30 percent, 50 percent, 70 percent and 100 percent. The calibration curve 19 of FIG. 10 is intended as a schematic and diagrammatic representation of the manner in which a hydrophobic standard means comprising a plurality of bodies may be employed and is not intended to represent a specific calibration curve for any specific instrument.

As described to this point, the present invention has been directed particularly to the calibration of a surface gauge 11 through use of a standard or standards 10. However, the present invention equally contemplates the calibration of a depth gauge 21 through the use of a standard or standards 20 (FIGS. 2 and 9). Due to the substantial similarities in the standards and procedures, the description given above will not be repeated in full detail. Instead, reference characters of a twenties order of magnitude and corresponding to those of the tens order of magnitude used hereinabove have been applied to corresponding portions in FIGS. 2 and 9 and the description given herein will be directed only to the distinctions between the standard 20 of FIGS. 2 and 9 and the standard 10 of FIGS. 1 and 8. Where the standard 10 of FIGS. 1 and 8 is provided with a planar surface 12 for receiving a gauge 11 undergoing calibration, the standard 20 of FIGS. 2 and 9 is provided with a bore 30 extending thereinto for receiving the penetrating probe 31 of the depth gauge 21.

As will be appreciated by persons knowledgeable in the calibration of nuclear radiation moisture gauges from the description given above, the present invention has for the first time provided a reliable calibration standard which is hydrophobic and not subject to fluctuation in effective "moisture content." This is achieved through the use of moderating and non-moderating material having little or no affinity for moisture, with the moderating material preferably being a hydrocarbon polymer containing hydrogen in the molecular structure thereof. Due to use of the moderating and non-moderating materials in interleaved superposed thin layers, the standard in accordance with the present invention has physical characteristics effective for representing a mass of homogeneous hydrogen content to a nuclear gauge undergoing calibration. As used, the standards have physical dimensions effective for representing an infinite mass to a nuclear gauge undergoing calibration and, where a plurality of bodies are provided, may be used to determine a plurality of points along a calibration curve.

In the drawings and specification, there has been set forth a preferred embodiment of the invention, and although specific terms are employed, they are used in a generic and descriptive sense only and not for purposes of limitation.

That which is claimed is:

1. A hydrophobic calibration standard for thermal neutron moisture gauges comprising at least one body formed of a moderating material containing hydrogen in the molecular structure thereof and a substantially non-moderating material, with the materials arranged for a substantially uniform distribution of moderating material throughout the at least one body so as to impart thereto physical characteristics effective for representing a mass of homogenous hydrogen content to a gauge undergoing calibration.

2. A standard means according to claim 1 having physical dimensions effective for representing an infinite mass to a gauge undergoing calibration.

3. A standard means according to claim 1 comprising a body of material having a planar surface for receiving a surface gauge.

4. A standard means according to claim 1 comprising a body of material having a bore therein for receiving a depth gauge.

5. A hydrophobic standard means for calibrating thermal neutron moisture gauges comprising a plurality of bodies each effective for representing a corresponding, discrete hydrogen content to a gauge undergoing calibration for thereby providing a corresponding plurality of calibration points.

6. A hydrophobic calibration standard for nuclear radiation moisture gauges comprising a body of superposed interleaved thin layers of a moderating material containing hydrogen in the molecular structure thereof and of a substantially non-moderating material.

7. A standard according to claim 6 wherein said layers of moderating and non-moderating material have a substantially constant, substantially uniform thickness.

8. A standard according to claim 7 wherein said layers of moderating material alternate with said layers of non-moderating material for sandwiching layers of one material between pairs of layers of the other material.

9. A standard according to claim 7 wherein the number of layers of one material is a multiple of the number of layers of the other material for sandwiching layers of the other material between sets of multiple adjacent layers of the one material.

10. A standard according to claim 9 wherein the number of layers of non-moderating material is a multiple of the number of layers of moderating material.

11. A standard according to claim 6 wherein said layers of moderating material have a substantially constant, substantially uniform first thickness and said layers of non-moderating material have a substantially constant, substantially uniform second thickness differing from said first thickness.

12. A standard according to claim 6 wherein said moderating material is a polymer film and said non-moderating material is a metal sheet.

13. A standard according to claim 12 wherein said moderating material is a hydrocarbon polymer film.

14. A standard according to claim 6 further comprising fastener means for clamping said layers into engagement.

15. A hydrophobic calibration standard for nuclear radiation moisture gauges comprising a plurality of thin layers of a hydrocarbon polymer effective for moderating neutrons, a plurality of thin layers of a non-moderating material arranged in interleaved superposed relation with said polymer layers, and fastener means for clamping said layers into engagement, said layers together forming a body having physical characteristics and dimensions effective for representing to a nuclear gauge undergoing calibration an infinite mass of homogeneous hydrogen content.

16. A standard according to claim 15 wherein said polymer layers are of polyethylene and said non-moderating layers are of magnesium.

* * * * *